US011399969B2

(12) United States Patent
Senness et al.

(10) Patent No.: US 11,399,969 B2
(45) Date of Patent: *Aug. 2, 2022

(54) STENT DELIVERY SYSTEM

(71) Applicant: Covidien LP, Mansfield, MA (US)

(72) Inventors: Charles Senness, Minnetonka, MN (US); John White, Lakeville, MN (US); Wanda Dent, Chanhassen, MN (US)

(73) Assignee: COVIDIEN LP, Mansfield, MA (US)

( * ) Notice: Subject to any disclaimer, the term of this patent is extended or adjusted under 35 U.S.C. 154(b) by 646 days.

This patent is subject to a terminal disclaimer.

(21) Appl. No.: 15/980,465

(22) Filed: May 15, 2018

(65) Prior Publication Data

US 2018/0256375 A1 Sep. 13, 2018

Related U.S. Application Data

(63) Continuation of application No. 14/256,136, filed on Apr. 18, 2014, now Pat. No. 10,016,292.

(51) Int. Cl.
*A61F 2/95* (2013.01)
*A61F 2/966* (2013.01)

(52) U.S. Cl.
CPC .............. *A61F 2/95* (2013.01); *A61F 2/966* (2013.01); *A61F 2/9517* (2020.05); *A61F 2/9522* (2020.05)

(58) Field of Classification Search
CPC ...... A61F 2/95; A61F 2/966; A61F 2002/011; A61F 2002/9517; A61F 2002/9522;

(Continued)

(56) References Cited

U.S. PATENT DOCUMENTS 5,391,172 A    2/1995  Williams et al.
5,397,304 A *  3/1995  Truckai ............. A61M 25/0138
                                                    604/528

(Continued)

FOREIGN PATENT DOCUMENTS

CN    103096844 A    5/2013
CN    103298433 A    9/2013

(Continued)

OTHER PUBLICATIONS

Notification of Rejection, and translation thereof, from counterpart Japanese Application No. 2016-562540, dated Jan. 15, 2019, 13 pp.

(Continued)

*Primary Examiner* — Martin T Ton
(74) *Attorney, Agent, or Firm* — Shumaker & Sieffert, P.A.

(57) ABSTRACT

A stent delivery system includes a handle and an elongate catheter extending from the handle. The elongate catheter includes an inner member, an outer member mounted about the inner member and adapted for longitudinal movement relative to the inner member from an extended position to a retracted position and a stent mounted about the inner member. The stent delivery system also includes a thumbwheel mounted to the handle. The thumbwheel is adapted for rotational movement to cause corresponding movement of the outer member from the extended position to the retracted position. In some examples, the stent delivery system may include a lock member adapted to engage at least one of the outer member and the thumbwheel to prevent movement thereof when the lock member is secured relative to the handle.

19 Claims, 9 Drawing Sheets

(58) Field of Classification Search
CPC ............ A61F 2002/9665; A61F 9/2427; A61F 9/243; A61F 9/2436; A61M 25/01; A61M 25/0113; A61M 25/0136
USPC ...................................................... 623/1.11
See application file for complete search history.

(56) References Cited

U.S. PATENT DOCUMENTS

| | | |
|---|---|---|
| 5,415,664 A | 5/1995 | Pinchuk |
| 5,458,615 A | 10/1995 | Klemm et al. |
| 5,480,423 A | 1/1996 | Ravenscroft et al. |
| 5,571,135 A | 11/1996 | Fraser et al. |
| 5,571,168 A | 11/1996 | Toro |
| 5,591,172 A | 1/1997 | Bachmann et al. |
| 5,690,643 A | 11/1997 | Wijay |
| 5,702,418 A | 12/1997 | Ravenscroft |
| 5,707,376 A | 1/1998 | Kavteladze et al. |
| 5,709,703 A | 1/1998 | Lukic et al. |
| 5,733,267 A | 3/1998 | DelToro |
| 5,772,669 A | 6/1998 | Vrba |
| 5,776,142 A | 7/1998 | Gunderson |
| 5,788,707 A | 8/1998 | Del Toro et al. |
| 5,800,517 A | 9/1998 | Anderson et al. |
| 5,824,058 A | 10/1998 | Ravenscroft et al. |
| 5,968,052 A | 10/1999 | Sullivan, III et al. |
| 6,042,588 A | 3/2000 | Munsinger et al. |
| 6,077,295 A | 6/2000 | Limon et al. |
| 6,077,297 A | 6/2000 | Robinson et al. |
| 6,120,522 A | 9/2000 | Vrba et al. |
| 6,123,723 A | 9/2000 | Konya et al. |
| 6,136,006 A | 10/2000 | Johnson et al. |
| 6,146,415 A | 11/2000 | Fitz |
| 6,183,481 B1 | 2/2001 | Lee et al. |
| 6,214,036 B1 | 4/2001 | Letendre et al. |
| 6,221,097 B1 | 4/2001 | Wang et al. |
| 6,241,758 B1 | 6/2001 | Cox |
| 6,251,132 B1 | 6/2001 | Ravenscroft et al. |
| 6,280,465 B1 | 8/2001 | Cryer |
| 6,302,893 B1 | 10/2001 | Limon et al. |
| 6,322,586 B1 | 11/2001 | Monroe et al. |
| 6,342,066 B1 | 1/2002 | Toro et al. |
| 6,350,278 B1 | 2/2002 | Lenker et al. |
| 6,368,344 B1 | 4/2002 | Fitz |
| 6,380,457 B1 | 4/2002 | Yurek et al. |
| 6,383,211 B1 | 5/2002 | Staehle |
| 6,391,051 B2 | 5/2002 | Sullivan, III et al. |
| 6,395,017 B1 | 5/2002 | Dwyer et al. |
| 6,478,819 B2 | 11/2002 | Moe |
| 6,500,202 B1 | 12/2002 | Shaolian et al. |
| 6,520,989 B1 | 2/2003 | Eaton |
| 6,562,063 B1 | 5/2003 | Euteneuer et al. |
| 6,576,006 B2 | 6/2003 | Limon et al. |
| 6,582,460 B1 | 6/2003 | Cryer |
| 6,623,518 B2 | 9/2003 | Thompson et al. |
| 6,626,934 B2 | 9/2003 | Blaeser et al. |
| 6,656,212 B2 | 12/2003 | Ravenscroft et al. |
| 6,669,716 B1 | 12/2003 | Gilson et al. |
| 6,676,693 B1 | 1/2004 | Belding et al. |
| 6,699,274 B2 | 3/2004 | Stinson |
| 6,736,839 B2 | 5/2004 | Cummings |
| 6,743,210 B2 | 6/2004 | Hart et al. |
| 6,749,627 B2 | 6/2004 | Thompson et al. |
| 6,755,854 B2 | 6/2004 | Gillick et al. |
| 6,786,918 B1 | 9/2004 | Krivoruchko et al. |
| 6,843,802 B1 | 1/2005 | Villalobos et al. |
| 6,866,669 B2 | 3/2005 | Buzzard et al. |
| 6,884,259 B2 | 4/2005 | Tran et al. |
| 6,911,039 B2 | 6/2005 | Shiu et al. |
| 6,939,352 B2 | 9/2005 | Buzzard et al. |
| 6,984,244 B2 | 1/2006 | Perez et al. |
| 7,074,236 B2 | 7/2006 | Rabkin et al. |
| 7,105,016 B2 | 9/2006 | Shiu et al. |
| 7,172,617 B2 | 2/2007 | Colgan et al. |
| 7,175,650 B2 | 2/2007 | Ruetsch |
| 7,201,769 B2 | 4/2007 | Jones et al. |
| 7,278,998 B2 | 10/2007 | Gaschino et al. |
| 7,285,130 B2 | 10/2007 | Austin |
| 7,303,580 B2 | 12/2007 | Parker |
| 7,338,518 B2 | 3/2008 | Chobotov |
| 7,381,216 B2 | 6/2008 | Buzzard et al. |
| 7,387,640 B2 | 6/2008 | Cummings |
| 7,419,501 B2 | 9/2008 | Chiu et al. |
| 7,435,253 B1 | 10/2008 | Hartley et al. |
| 7,468,070 B2 | 12/2008 | Henry et al. |
| 7,473,271 B2 | 1/2009 | Gunderson |
| 7,476,244 B2 | 1/2009 | Buzzard et al. |
| 7,491,224 B2 | 2/2009 | Cox et al. |
| 7,550,001 B2 | 6/2009 | Dorn et al. |
| 7,553,322 B2 | 6/2009 | Dorn et al. |
| 7,608,099 B2 | 10/2009 | Johnson et al. |
| 7,651,519 B2 | 1/2010 | Dittman |
| 7,651,521 B2 | 1/2010 | Ton et al. |
| 7,674,282 B2 | 3/2010 | Wu et al. |
| 7,740,652 B2 | 6/2010 | Gerdts et al. |
| 7,758,624 B2 | 7/2010 | Dorn et al. |
| 7,758,625 B2 | 7/2010 | Wu et al. |
| 7,780,716 B2 | 8/2010 | Pappas et al. |
| 7,780,717 B2 | 8/2010 | Ducke et al. |
| 7,794,487 B2 | 9/2010 | Maiercak et al. |
| 7,799,065 B2 | 9/2010 | Pappas |
| 7,815,669 B2 | 10/2010 | Matsuoka et al. |
| 7,819,882 B2 | 10/2010 | Rourke |
| 7,867,268 B2 | 1/2011 | Shelso |
| 7,993,388 B2 | 8/2011 | Lee et al. |
| 2005/0060016 A1* | 3/2005 | Wu ............................ A61F 2/95 623/1.11 |
| 2005/0090890 A1 | 4/2005 | Wu et al. |
| 2006/0259124 A1* | 11/2006 | Matsuoka ............... A61F 2/966 623/1.12 |
| 2006/0282150 A1 | 12/2006 | Olson et al. |
| 2007/0060999 A1 | 3/2007 | Randall et al. |
| 2007/0073389 A1 | 3/2007 | Bolduc et al. |
| 2007/0088421 A1 | 4/2007 | Loewen |
| 2007/0156222 A1 | 7/2007 | Feller et al. |
| 2007/0168014 A1 | 7/2007 | Jimenez et al. |
| 2007/0219617 A1 | 9/2007 | Saint |
| 2009/0210046 A1* | 8/2009 | Shumer ...................... A61F 2/95 623/1.11 |
| 2010/0036472 A1 | 2/2010 | Papp |
| 2010/0145431 A1 | 6/2010 | Wu et al. |
| 2012/0123516 A1 | 5/2012 | Gerdts et al. |
| 2013/0013049 A1* | 1/2013 | Melsheimer ............... A61F 2/95 623/1.12 |
| 2013/0018451 A1 | 1/2013 | Grabowski et al. |
| 2013/0178930 A1 | 7/2013 | Straubinger et al. |

FOREIGN PATENT DOCUMENTS

| | | |
|---|---|---|
| JP | 2008513180 A | 5/2008 |
| JP | 2009523490 A | 6/2009 |
| JP | 2014501559 A | 1/2014 |
| WO | 2007005799 A1 | 1/2007 |
| WO | 2007084370 A1 | 7/2007 |
| WO | 2011144351 A2 | 11/2011 |

OTHER PUBLICATIONS

Second Office Action, and translation thereof, from counterpart Chinese Application No. 201580020350.7, dated Dec. 7, 2018, 11 pp.
Invitation to Pay Additional Fees and Partial Search Report from counterpart International Application No. PCT/US2015/025848, dated Sep. 22, 2016, 6 pp.
International Search Report and Written Opinion of counterpart International Application No. PCT/US2015/025848, dated Oct. 14, 2016, 5 pp.
International Preliminary Report on Patentability from International Application No. PCT/US2015/025848, dated Oct. 18, 2016, 9 pp.
First Office Action and Search Report, and translation thereof, from counterpart Chinese Application No. 201580020350.7, dated Apr. 20, 2018, 17 pp.

(56) References Cited

OTHER PUBLICATIONS

Communication Pursuant to Rules 161(1) and 162 EPC, dated Nov. 25, 2016 from counterpart European Application No. 15719083.6, 2 pp.
Prosecution History from U.S. Appl. No. 14/256,136, dated Apr. 12, 2016 through Feb. 14, 2018, 170 pp.

* cited by examiner

STENT DELIVERY SYSTEM

This application is a continuation of U.S. patent application Ser. No. 14/256,136, filed Apr. 18, 2014, and entitled, "STENT DELIVERY SYSTEM," the entire content of which is incorporated by reference herein.

BACKGROUND

Technical Field

The present disclosure generally relates to a system and method for delivering and deploying a medical device within a vessel and, more particularly, relates to a system and method for delivering and deploying a stent within the vasculature of a patient, particularly, the venous system.

Description of Related Art

Stent delivery systems and associated methodologies to deliver a stent used for supporting vasculature are known in the art. One typical stent delivery system includes a balloon catheter and a stent positioned on the balloon of the catheter. The catheter is advanced within the vasculature to a targeted site and the balloon expanded to correspondingly expand the stent against the vessel wall. Another stent delivery system for a self-expanding stent includes inner and outer catheters. The stent is retained within the outer catheter in a constrained state and advanced to the targeted site. The outer catheter is thereafter retracted or the inner catheter advanced to expose the stent, which self-expands, for application against the vessel wall.

Stents for use in the venous system such as the inferior vena cava (IVC), common iliac, external iliac, and common femoral veins regions require high strength and maximum flexibility. In addition, these venous stents may be greater in length and in diameter than arterial stents, and, thus present additional obstacles in placement and deployment within the targeted vessel. Moreover, conventional delivery systems and designs for deploying arterial stents are not applicable in a venous application.

SUMMARY

Accordingly, the present disclosure is directed to further improvements for stent delivery systems, particularly, delivery systems for delivering a stent within the venous system of the subject. In one embodiment, a stent delivery system includes a handle and an elongate catheter extending from the handle, and defining a leading end and a trailing end, and having a longitudinal axis. The elongate catheter includes an inner member, an outer member mounted about the inner member and adapted for longitudinal movement relative to the inner member from an extended position to a retracted position, and a stent mounted about the inner member. A thumbwheel is mounted to the handle and operatively connected to the outer member. A lock member is releasably mountable to the handle. The thumbwheel is adapted for rotational movement to cause corresponding movement of the outer member from the extended position to the retracted position. The lock member is adapted to operatively engage at least one of the outer member and the thumbwheel to prevent movement thereof when the lock member is secured relative to the handle, and is adapted to operatively release the at least one of the outer member and the thumbwheel when the lock member is released relative to the handle.

In embodiments, the lock member is adapted to operatively engage each of the outer member and the thumbwheel to prevent respective movement thereof when the lock member is secured relative to the handle and adapted to operatively release each of the outer member and the thumbwheel when the lock member is released relative to the handle.

In some embodiments, an outer clip is secured to the outer member and a pull cable is operatively coupled to the outer clip and the thumbwheel. In embodiments, the outer clip includes a lock wall dimensioned to be engaged by the lock member when the lock member is secured relative to the handle to prevent longitudinal movement of the outer clip and the outer member. The lock member may include a leading clip restraint, which is engageable with the lock wall of the outer clip.

In some embodiments, the lock member includes a trailing thumbwheel constraint having a lock detent. The lock detent may be dimensioned and adapted to be received within a recess of the thumbwheel to prevent rotational movement of the thumbwheel when the lock member is secured relative to the handle.

In certain embodiments, the lock member includes a resilient lock spring. The lock spring may be releasably engageable with the handle, and adapted to transition between a lock position in which the lock member is secured to the handle and a release position in which the lock member is removable from the handle.

In some embodiments, a ratchet permits selective incremental movement of the thumbwheel in a first rotational direction corresponding toward the retracted position of the outer member while preventing rotational movement thereof in a second negative direction. The ratchet may include a ratchet spring mounted to the handle. The ratchet spring may be engageable with ratchet teeth defined within the thumbwheel.

In some embodiments, the outer clip may include at least one anti-rotation wing. The anti-rotation wing may be received within a channel of the handle and dimensioned to traverse the channel upon longitudinal movement of the outer clip. The at least one anti-rotation wing is dimensioned to prevent rotational movement of the outer member relative to the handle. In embodiments, the outer clip includes a pair of diametrically opposed anti-rotation wings received within corresponding channels of the handle.

In embodiments, the elongate catheter may include a stop member mounted about the inner member. The stop member is dimensioned to engage the stent upon movement of the outer member from the extended position to the retracted position to minimize movement of the stent.

In embodiments, the stent may be adapted to expand from a constrained condition when the outer member is in the extended position thereof to an expanded condition upon movement of the outer member toward the retracted position thereof.

In certain embodiments, an isolation sheath assembly is coaxially mounted about the outer member. The isolation sheath assembly may be fixed from longitudinal movement. In some embodiments, the isolation sheath assembly is mechanically secured to a strain relief. The strain relief may be releasably secured to the handle to permit release of the strain relief and the isolation sheath assembly from the handle.

In one embodiment, a stent delivery system includes a handle and an elongate catheter extending from the handle. The elongate catheter defines a leading end and a trailing end, and has a longitudinal axis. The elongate catheter includes an inner member, an outer member mounted about the inner member and adapted for longitudinal movement relative to the inner member from an extended position to a retracted position, a stent mounted about the inner member, an outer clip secured to the outer member and a pull cable operatively coupled to the outer clip. An actuator may be mounted to the handle and operatively connected to the pull cable. The actuator is adapted for movement relative to the handle to cause corresponding movement of the pull cable and the outer member from the extended position to the retracted position.

In embodiments, the outer clip includes at least one anti-rotation wing for preventing rotational movement of the outer member relative to the handle. In some embodiments, the at least one anti-rotation wing is dimensioned for reception within a corresponding wing receiving channel of the handle, and is adapted to traverse the channel during movement of the outer member toward the retracted position. In some embodiments, the outer clip includes first and diametrically opposed anti-rotation wings, which are received within respective corresponding channels of the handle.

In some embodiments, the outer clip includes a substantial cylindrical mount coaxially mounted relative to the outer member and a wire mounting head defining an opening for receiving the pull cable. The pull cable includes an enlarged general spherical member connected to an end of the pull cable. The general spherical member engages the outer clip to prevent passage of the pull cable through the opening of the wire mounting head during movement of the outer member toward the retracted position.

Embodiments can include one or more of the following advantages. The stent delivery system incorporates a deployment mechanism which provides a significant mechanical advantage in deployment of the stent. In particular, the deployment mechanism provides an increased velocity ratio thereby effecting efficient and rapid longitudinal translation of the outer member or sheath to expose the stent. This efficient translation of the outer sheath is advantageous in a venous application where the stent is enlarged in length and diameter of the stent. The stent delivery system also may be easily manipulated with the single hand of the clinician, and may be maneuvered to deploy the stent without concerns of affecting its functionality and operation.

Other aspects, features, and advantages will be apparent from the description, drawings, and the claims.

BRIEF DESCRIPTION OF THE DRAWINGS

Embodiments of the present disclosure will be readily appreciated by reference to the drawings wherein.

DESCRIPTION

Embodiments of the presently disclosed stent delivery system will now be described in detail with reference to the drawing figures wherein like reference numerals identify similar or identical elements. In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse or other care provider and may include support personnel.

Referring now to the drawings and, in particular to FIGS. 1-6, there is illustrated the stent delivery system 10 in accordance with the principles of the present disclosure. The stent delivery system 10 is adapted to deliver a stent, particularly, a self-expanding stent, within the vasculature of a subject. In particular applications, the stent delivery system 10 may be utilized to position a stent in the venous system of the subject including the inferior vena cava (IVC), common iliac, external iliac, and common femoral veins for chronic venous obstructions and/or May-Thurner syndrome. The stent may be fabricated from any suitable shape memory or super-elastic material such as nickel titanium (e.g., Nitinol). In embodiments, the super-elastic material is treated to cause the stent body to expand to its Austenitic memory state when released from a constrained condition to assume a predetermined deployed or expanded diameter. The stent may come in a variety of sizes and lengths. In a venous application, the stent may be 10 millimeters (mm), 12 mm, 14 mm, 16 mm, 18 mm or 20 mm in diameter, and 40 mm to 80 mm in length. Other diameters and lengths are also envisioned. Venous stents are typically greater in length and diameter relative to arterial stents, and thus present additional challenges in design and functioning of the associated stent delivery system 10.

One example of a self-expanding stent is disclosed in commonly assigned U.S. Pat. No. 7,993,388, the entire contents of which are incorporated herein. Alternatively, the stent delivery system may have application in the peripheral vasculature, coronary vasculature or neurovasculature, and/or may be used in any body vessel or duct.

Figure 2:
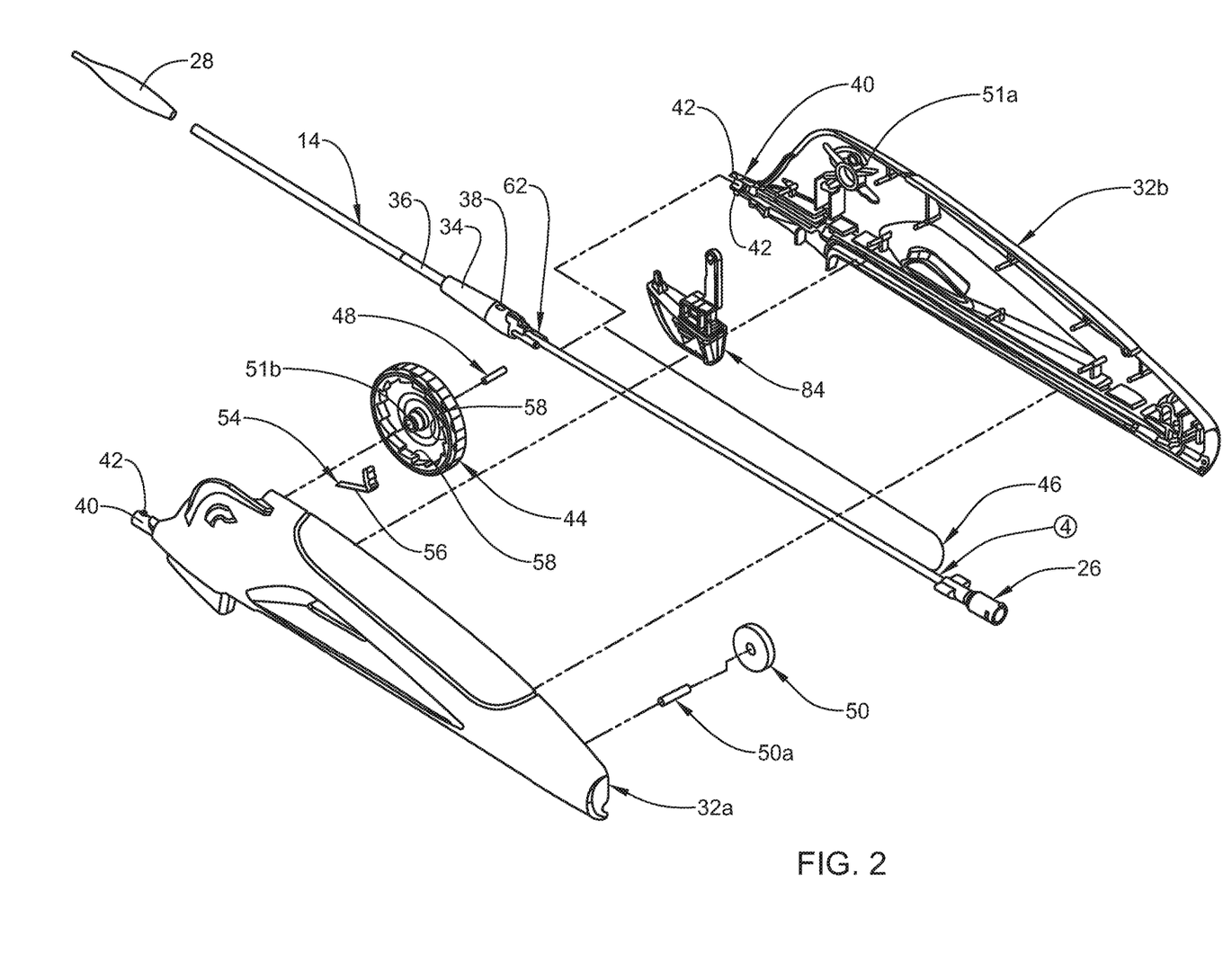
FIG. 2 is an exploded perspective view of the stent delivery system.
Figures 4, 5:
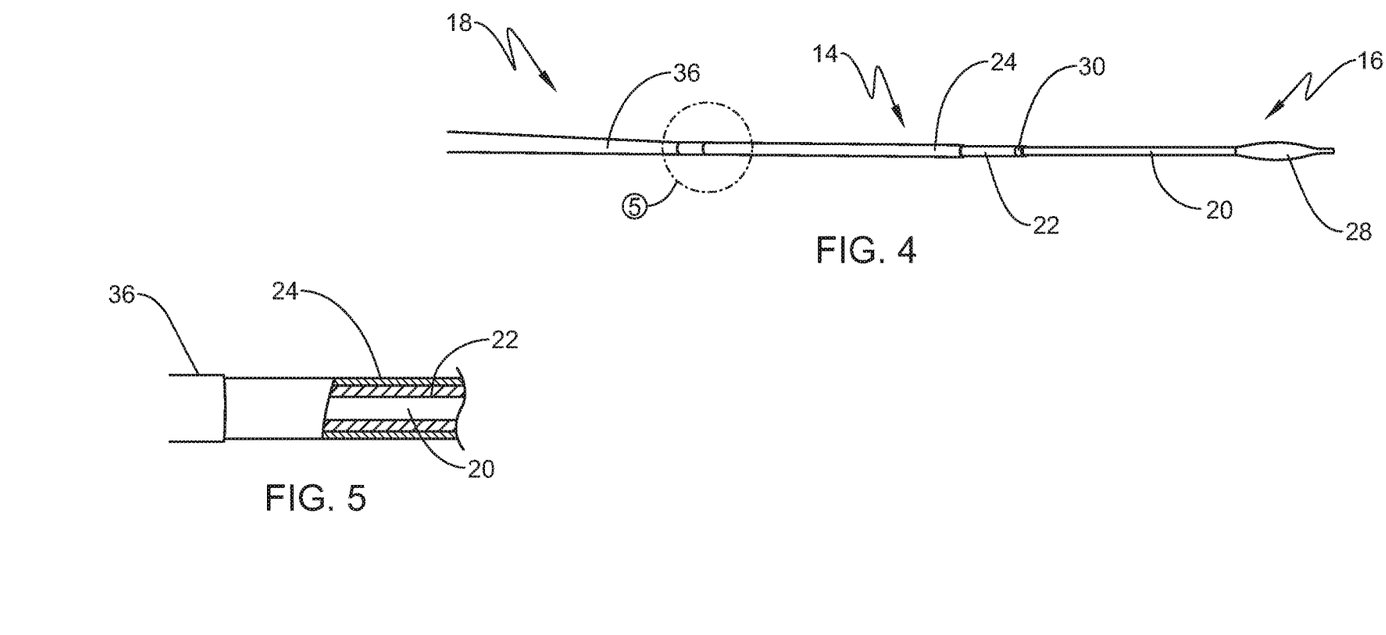
FIG. 4 is an enlarged isolated view of the area of detail identified in FIG. 3.
FIG. 5 is an enlarged isolated view of the area of detail identified in FIG. 4.
Figure 6:
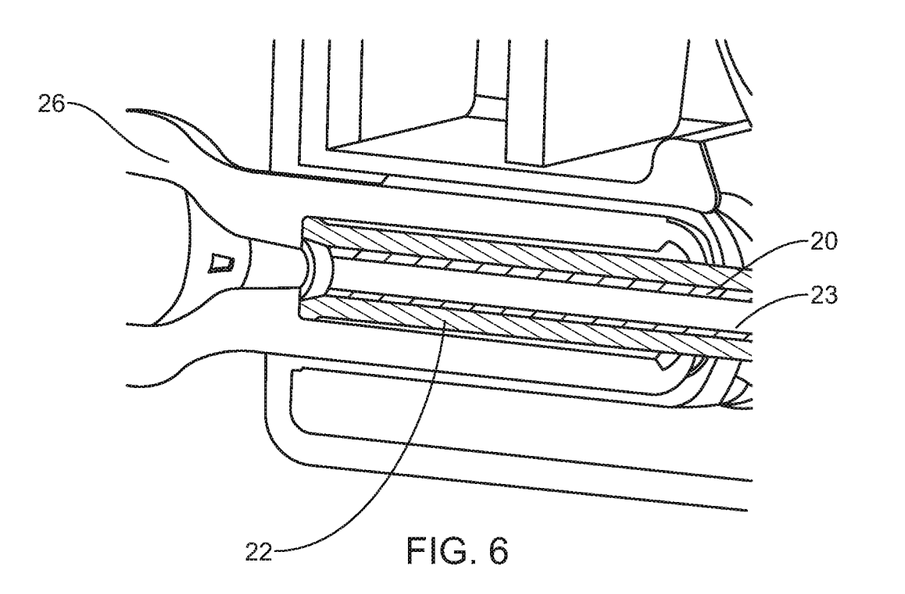
FIG. 6 is an enlarged sectional view illustrating the inner member and the stop member secured within the handle.

The stent delivery system 10 is contemplated as an over-the-wire single-handed deployment system for deploying a self-expanding stent. The stent delivery system 10 includes a handle 12 and an elongated catheter 14 extending from the handle 12. The elongated catheter 14 defines a longitudinal axis "k", and has leading or distal end 16 and trailing or proximal end 18. The catheter 14 includes an inner assembly or member 20, an intermediate or stop member 22 coaxially mounted about the inner member 20, and a retractable outer member 24 coaxially mounted about the inner member 20 and the stop member 22. As best depicted in FIGS. 2, 4 and 6, the inner member 20 extends through the handle 12 and is secured to a luer port or connector 26 mounted to the trailing or proximal end of the handle 12. The stop member 22 is also secured to the luer connector 26. Adhesives, cements, glues, welding connections, thermal bonding or insert moulding techniques may be used to secure the inner and stop members 22, 24 to the luer port 26. The inner member 20 defines a lumen 23 for reception and passage of a guidewire. The inner member 20 may be made of any suitable material such as, e.g., a braid reinforced polyimide/polytetrafluorethylene (PTFE) composite or an extruded polyetheretherketone (PEEK) material. Other materials are also contemplated.

Referring again, to FIGS. 1-3, a catheter tip 28 is mounted to the leading end of the inner member 20. The catheter tip 28 defines a narrow profile to facilitate advancement of the elongate catheter 14 through the vasculature. The catheter tip 28 may be a separate component connected to the inner member 20 through conventional means or be monolithically formed with the inner member 28. Radiopaque markers may be mounted to the inner member 20 to facilitate placement of the stent 16.

Figure 3:
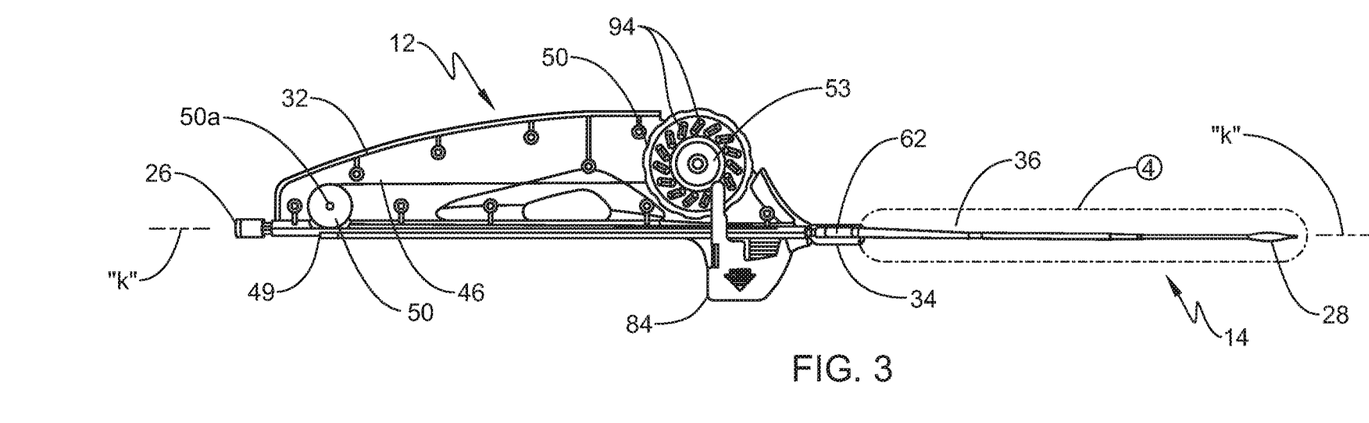
FIG. 3 is a side view in partial cross-sectional of the stent delivery system.
Figure 7:
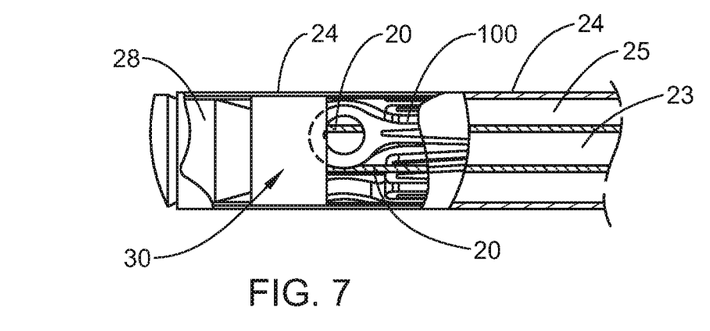
FIG. 7 is an enlarged isolated view of the area of detail identified in FIG. 1.

Referring to FIGS. 1-4 and 7, the outer member 24 is adapted for longitudinal movement relative to the longitudinal axis from an extended position depicted in FIG. 7 to the retracted position depicted in FIGS. 3 and 4. In the extended position, the outer member 24 at least partially overlaps the catheter tip 28 connected to the inner member 20. The outer member 24 and the inner member 20 define a space 25 therebetween defining a stent retaining region for accommodating the stent 100 as best depicted in FIG. 7. In FIG. 7, the proximal or trailing portion of the stent 100 is removed. The stent 100 is coaxially mounted about the inner member 20 adjacent the catheter tip 28 and is constrained in the initial condition by the outer member 24. The outer member 24 may include a radiopaque marker 30 adjacent its leading end. The outer member 24 may be made from any suitable material including, e.g., a braid reinforced Grilamid® polyamide with a PTFE liner. The liner may be coated with a silicon solution to aid in reducing friction between the inner and the outer members 20, 24 and/or stent 100. The stop member 22 is dimensioned to prevent longitudinal movement of the stent 100 during retracting movement of the outer member 24. The stop member 22 may have a radiopaque marker or band 30 at its leading or distal end to assist in stent placement.

Figure 1:
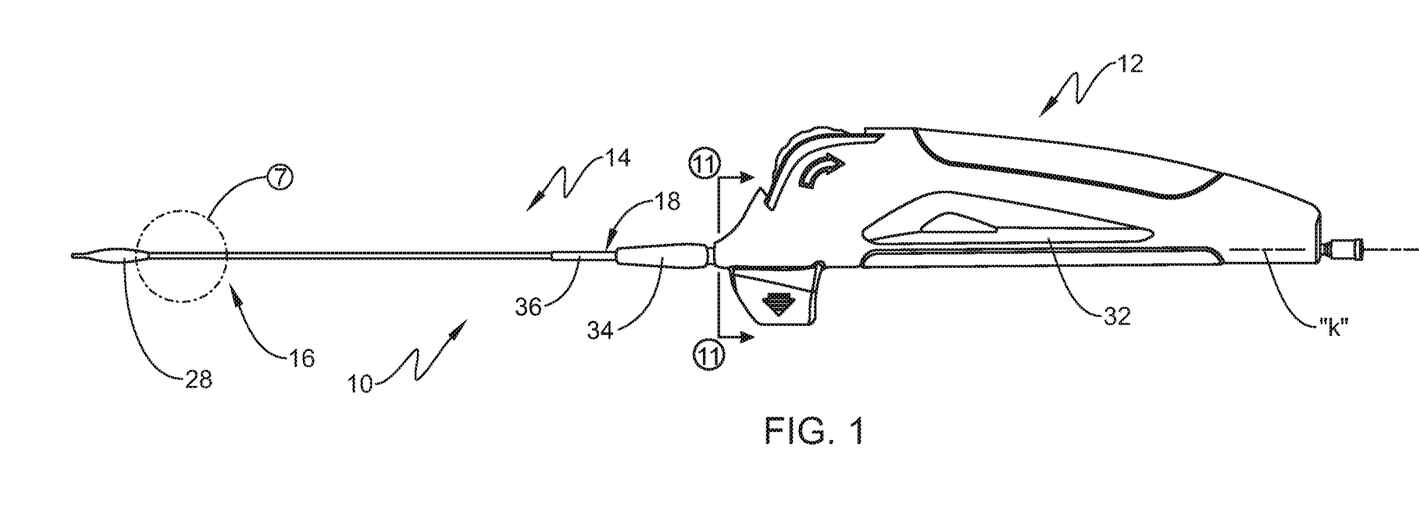
FIG. 1 is a side plan view of the stent delivery system in accordance with the principles of the present disclosure.

With reference to FIGS. 1-3, the handle 12 includes a handle frame or grip 32 consisting of handle sections 32a, 32b, a strain relief 34 mounted on one end of the handle frame 32 and an isolation sheath assembly 36 mechanically secured to the strain relief 34. The strain relief 34 may be releasably secured to the handle frame 32 to permit release of the strain relief 34 and the isolation sheath assembly 36 from the handle frame 32. As best depicted in FIG. 2, the strain relief 34 may include two diametrically opposed openings 38, which upon placement of the strain relief 34 over the strain relief mount 40 at the end of the handle frame 32, receive correspondingly opposed mounting projections 42 extending outwardly of the strain relief mount 40 to releasably secure the strain relief 34 and the isolation sheath assembly 36 to the frame 32. The isolation sheath assembly 36 surrounds, or is coaxially mounted about, the outer member 24 and extends to a location proximal of the stent retaining area of the outer member 24. The isolation sheath assembly 36 is stationary or fixed from longitudinal movement, and isolates the movement of the outer member 24 from the surrounding vasculature. The isolation sheath assembly 36 may be fabricated, from any suitable material including, e.g., a coil reinforced polyimide/PTFE composite or an extruded high density polyethylene (HDPE).

The handle 12 contains an actuator or thumbwheel 44 which is rotatably mounted to the handle frame 32 via integrally molded hubs 51a, 51b associated with the handle frame 32 (e.g., each of handle sections 32a, 32b) and the thumbwheel 44 (e.g., on each side of the thumbwheel 44), respectively. A pull cable 46 is operatively coupled to the thumbwheel 44 via pin 48. In embodiments, the end of the pull cable 46 is secured to the pin 48 including adhesives, a press fit or other suitable arrangements. The pull cable 46 is wrapped about hub 53 (FIG. 3) which is integral with the thumbwheel 44, and extends about a pulley 50 (rotatably mounted about pin 50a) within the handle frame 32. The pull cable 46 terminates within the handle 12 where it is connected to the outer member 24 in a manner to be discussed hereinbelow. The thumbwheel 44 is rotated to pull the pull cable 48 to retract the outer member 24 in a proximal direction to uncover and release the stent 100.

The deployment mechanism including, e.g., the pulley 50, hub 53 and pull cable 48, provide significant mechanical advantages in retracting the outer member 24 to uncover and release the stent 100. The pulley 50 and hub 53 provide an enhanced velocity ratio thereby increasing the speed and displacement distance of the outer member 24 in the longitudinal retracting direction upon incremental rotation of the thumbwheel 44. This increase velocity ratio is advantageous in deployment of a relatively large venous stent 100 in, e.g., a venous application, and substantially minimizes stent jumping during deployment. In embodiments, the distance between the center of the hub 53 and the pulley 50 ranges from about 5 inches to 7 inches, preferably, about 6 inches. The diameter of the pulley 50 and hub 53 range from about 0.25 inches to about 0.50 inches, preferably about 0.25 inches.

Figure 8:
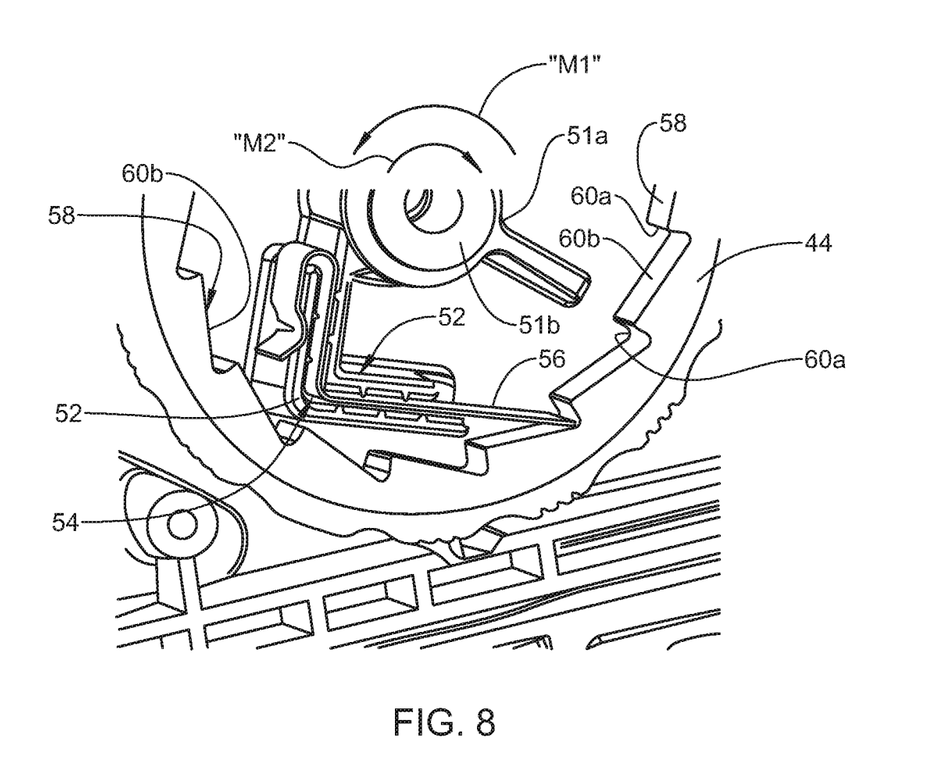
FIG. 8 is an enlarged view of the thumbwheel and the ratchet within the handle.
Figure 9A:
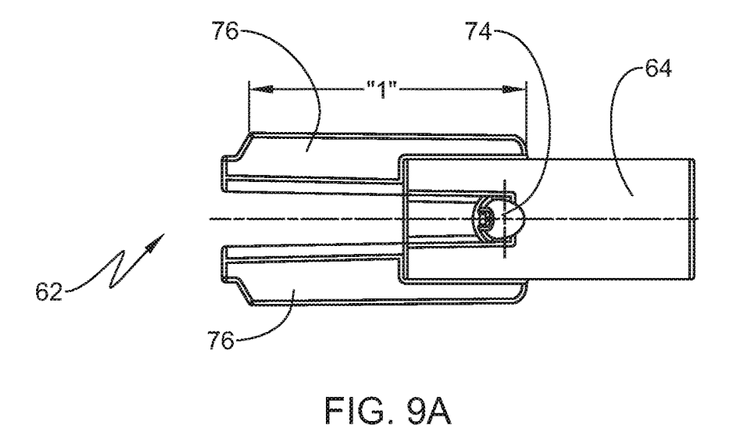
FIGS. 9A-9D are views of the outer clip for securing the outer member.
Figure 9B:
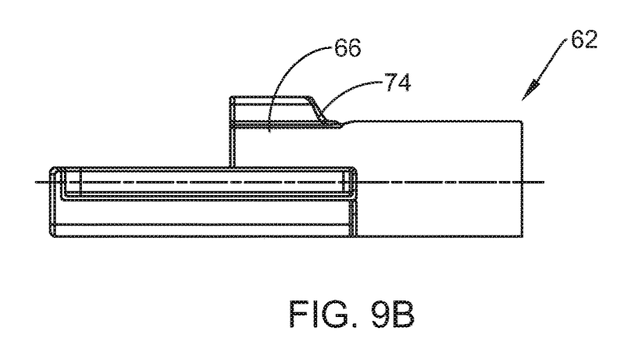
Figure 9C:
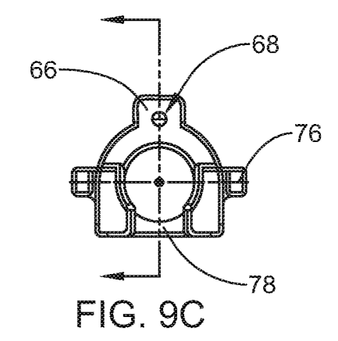
Figure 9D:
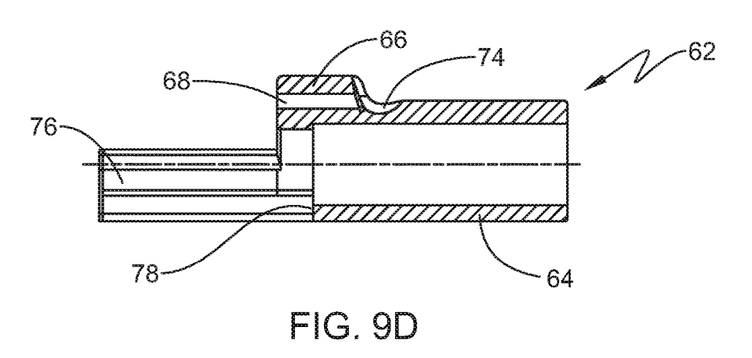
Figure 10A:
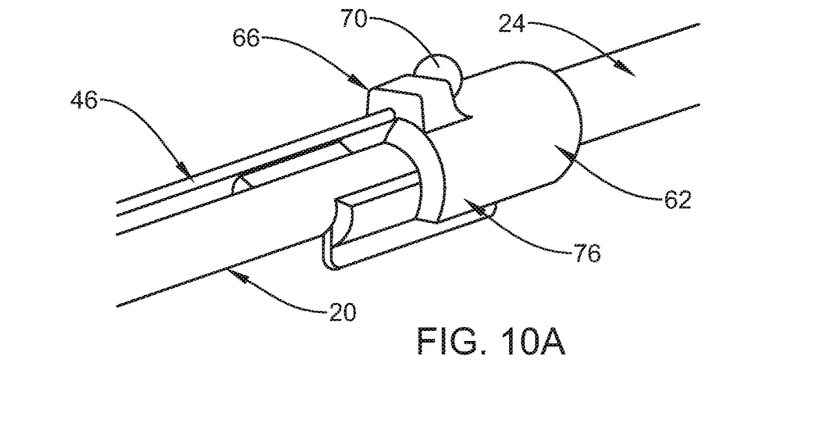
FIGS. 10A-10C are perspective, side plan and side cross-sectional views illustrating the outer clip secured to the outer member and the pull cable.
Figure 10B:
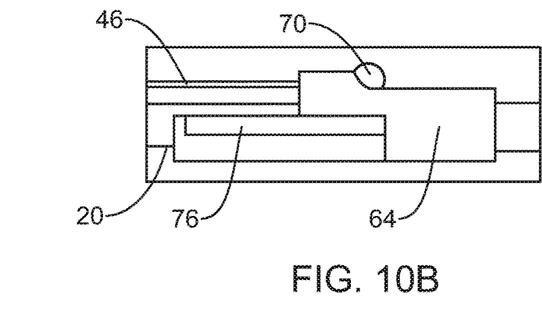
Figure 10C:
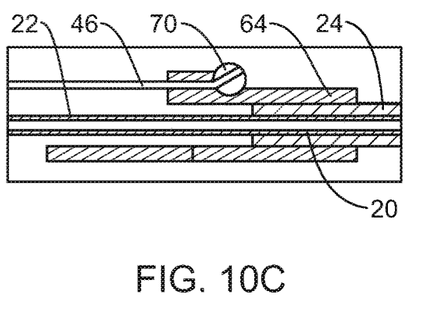

Referring now to FIGS. 2 and 8, the handle 12 includes a spring biased ratchet to permit selective incremental movement of the thumbwheel 44 in a first rotational direction "$m_1$" corresponding to the retracting movement of the outer member 24 while preventing rotational movement thereof in a second negative direction "$m_2$". In one embodiment, the handle section 32a includes a spring channel or mount 52 which receives a ratchet spring 54 in secured relation therewith. The ratchet spring 54 includes a depending ratchet leg 56 which extends outwardly toward the circumferential area of the thumbwheel 44. One side of the thumbwheel 44 defines a circumferential array of ratchet teeth 58. The ratchet teeth 58 each may define a lock surface 60a and an inclined surface 60b. During rotational movement of the thumbwheel 44, the ratchet leg 56 of the ratchet spring 54 rides on the inclined surface 60b, whereby upon clearing same, returns outwardly to its normal condition to engage the lock surface 60a of the respective tooth 58 of the array thereby preventing negative rotation of the thumbwheel 44. The ratchet spring 54 may also provide an audible confirmation of retracting movement of the outer member 24.

Referring now to FIGS. 9A-9D and FIGS. 10A-10C, in conjunction with FIGS. 2 and 3, the mechanism for connecting the outer member 24 to the pull cable 48 will be discussed. The outer member 24 has an outer clip 62 mounted to the trailing or proximal end of the outer member 24. The outer clip 62 includes a leading cylindrical mount 64 which receives the trailing end of the outer member 24 in, e.g., coaxial arrangement therewith. The two components are secured to each other with the use of glue (e.g., UV curable glue), adhesives, cements, welding, insert moulding, thermal bonding or other suitable arrangements. The outer clip 62 further includes a wire mounting head 66 defining an opening 68 for receiving the pull cable 46. The end of the pull cable 46 includes a ball or general spherical member or segment 70 from which the pull cable 46 extends back toward the pulley 50. The ball segment 70 prevents the pull cable 46 from sliding through the outer clip 62 when the pull cable 46 is pulled in the proximal or trailing direction corresponding to retracting movement of the outer member 24. The ball segment 70 is dimensioned to mechanically lock with a corresponding recessed surface 74 of the outer clip 62. In embodiments, the ball segment 70 is secured to the outer clip 62 with a mechanical interlock and/or adhesives, or through welding, swaging or insert molding.

Figure 11:
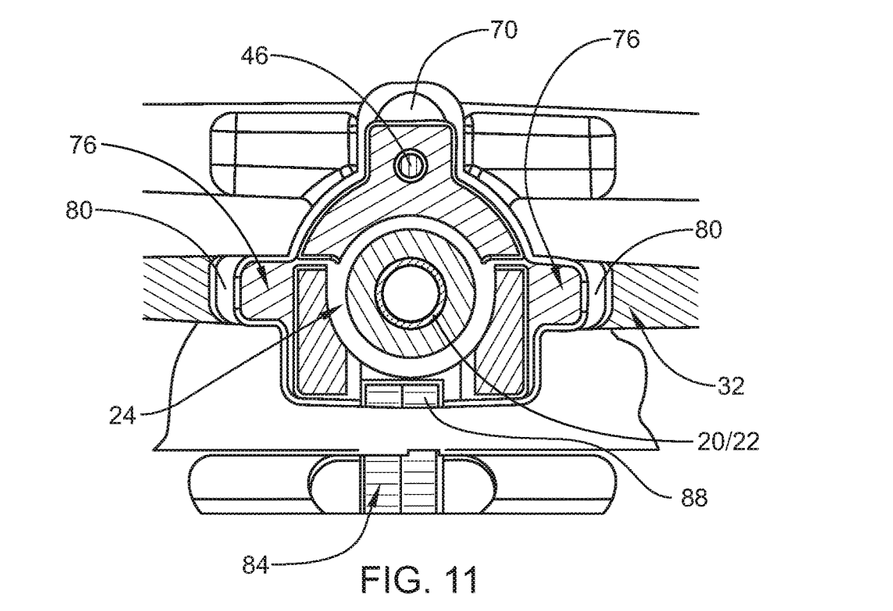
FIG. 11 is a cross-sectional view taken along the lines 11-11 of FIG. 1.
Figure 12:
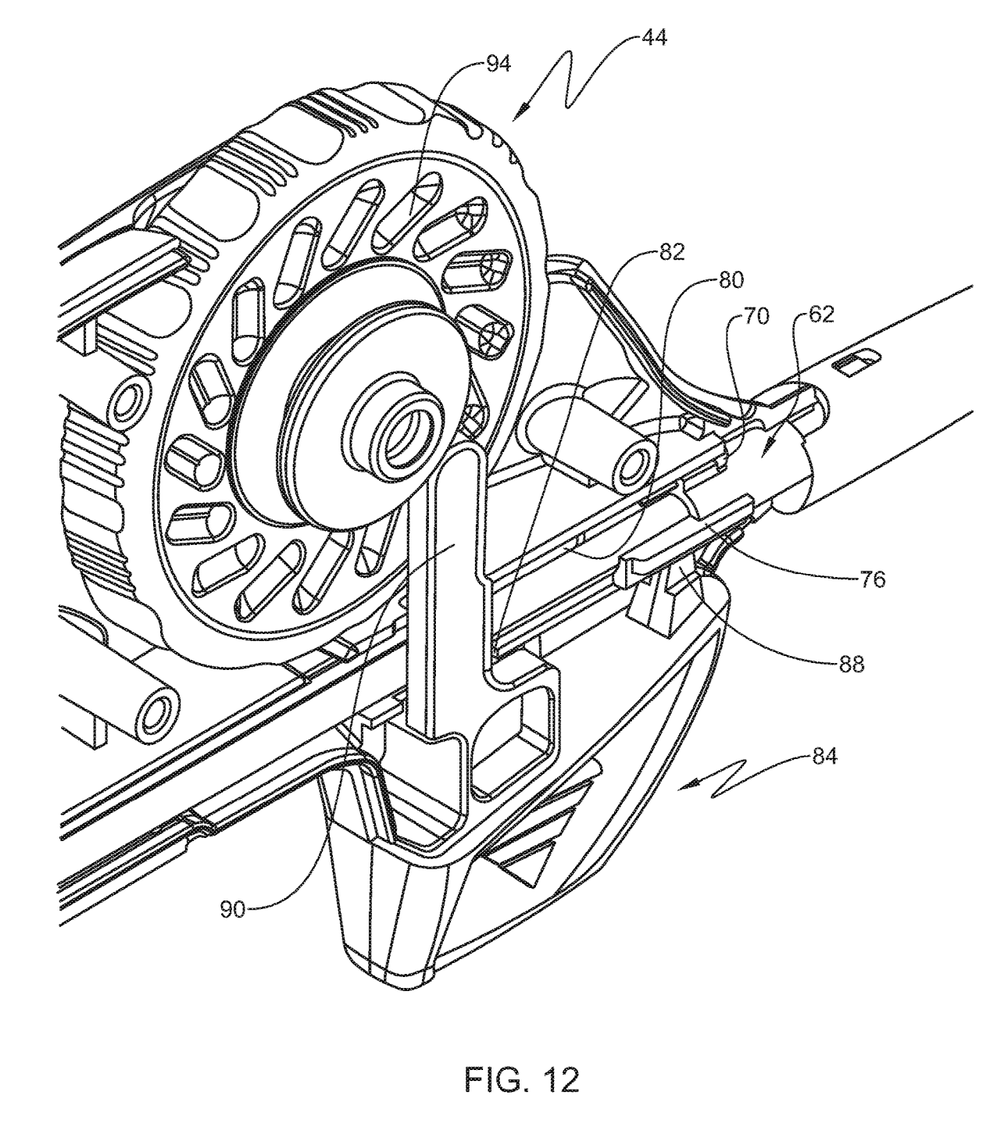
FIG. 12 is a partial perspective view of the handle with portions removed illustrating the lock member for securing the thumbwheel and the outer member.
Figure 13:
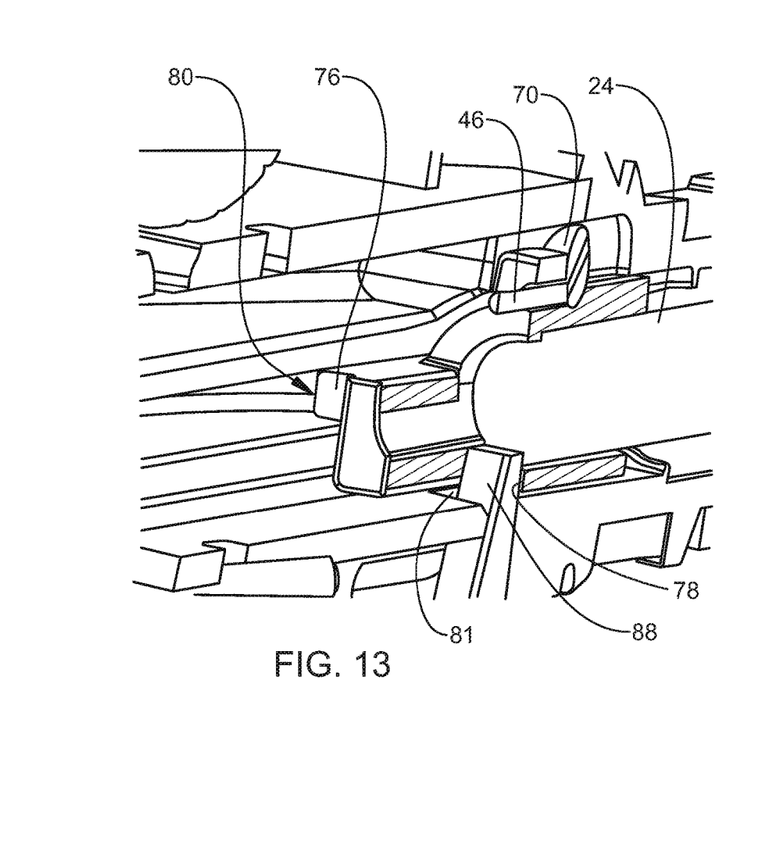
FIG. 13 is a perspective view illustrating the lock member securing the outer clip.
Figure 14:
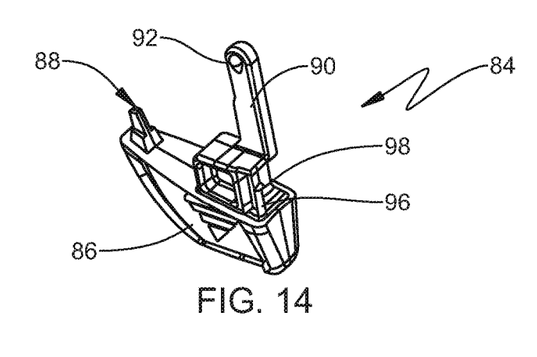
FIG. 14 is a perspective view of the lock member.
Figure 15:
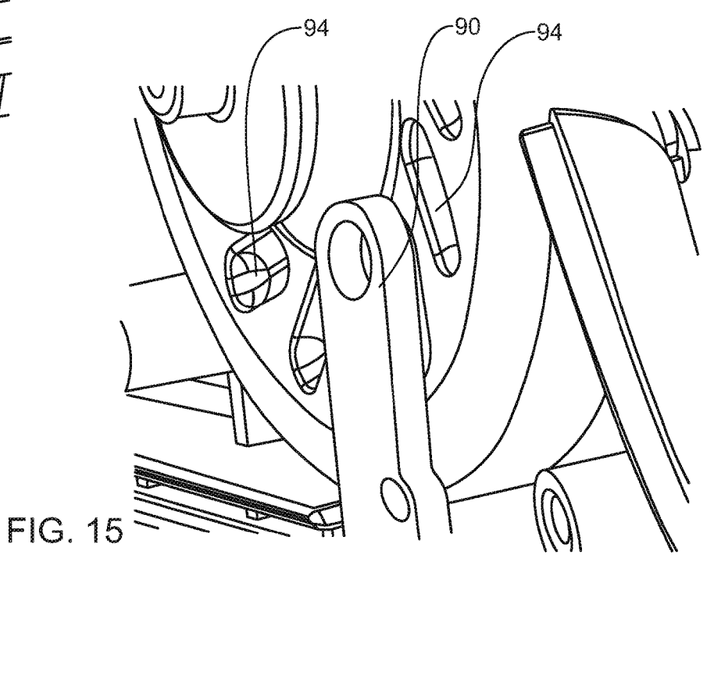
FIG. 15 is a perspective view illustrating the lock member securing the thumbwheel.

The outer clip 62 further includes a pair of diametrically opposed anti-rotation wings 76 and a lower lock wall 78 defined between the wings 76. The anti-rotation wings 76 are received within correspondingly dimensioned wing receiving channels 80 (FIGS. 11-13) formed in the handle sections 32a, 32b. The wings 76 traverse the channels 80 during retracting movement of the pull cable 46 and the outer member 24. With this arrangement, the outer clip 62 is constrained to travel solely in a longitudinal direction and is not capable of rotating relative to the handle 12. This eliminates the potential of the pull cable 46 wrapping about the inner member 20 or any of the components within the handle 12 and, also, reduces the risk of non deploy or partial deploy of the stent 100. Furthermore, through this arrangement, the clinician may rotate the handle 12 (which causes corresponding rotation of the outer member 24) during use without concern of the pull cable 46 wrapping around the inner member 20 or the stop member 22, e.g., without affecting the functioning of these components. The wings 76 each define a longitudinal length "l" (FIG. 9A) which is greater than the length of a gap 82 (FIGS. 2 and 12) extending through approximately the handle frame 32 and through at least one of the channels 80 to ensure the wings 76 remain within the channels 80 during traversing movement. The purpose of the gap 82 will be discussed hereinbelow.

Referring now to FIGS. 2 and 12-14, the lock member 84 will be discussed. In general, the lock member 84 is adapted to secure the thumbwheel 44 and the outer member 24 during transit and/or prior to use. The lock member 84 is releasably mounted to the handle frame 32. In one embodiment, the lock member 84 includes a manually engageable segment 86 extending beneath the handle 12, a leading clip constraint 88 and a trailing thumbwheel constraint 90. In the assembled condition of the lock member 84 relative to the handle 12, the leading clip constraint 88 extends through gap 81 within the handle frame 32 (FIG. 13) and engages the lower lock wall 78 (FIGS. 9D and 13) of the outer clip 62 to prevent retracting movement of the outer member 24 during transit and/or prior to use (see FIGS. 11-13).

Figure 16:
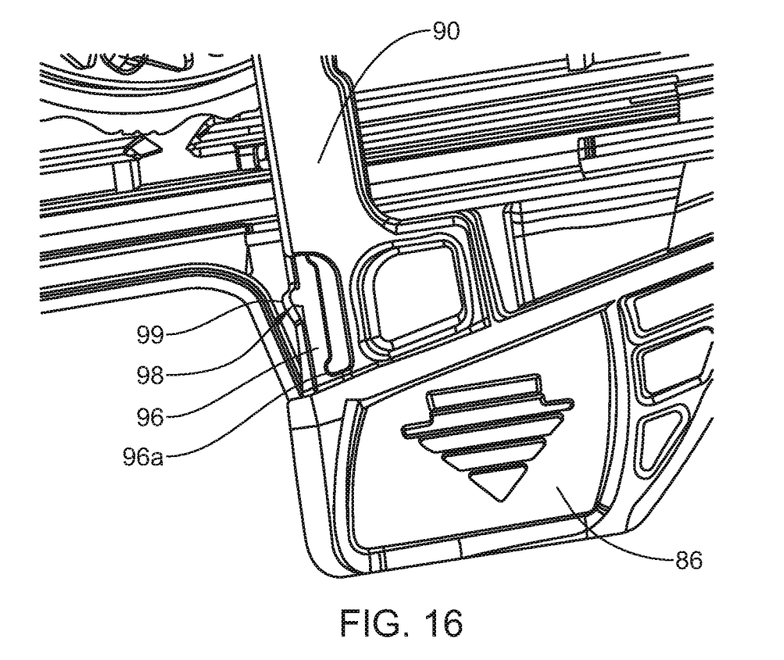
FIGS. 16 and 17 are views illustrating the lock member in secured and released conditions relative to the handle.
Figure 17:
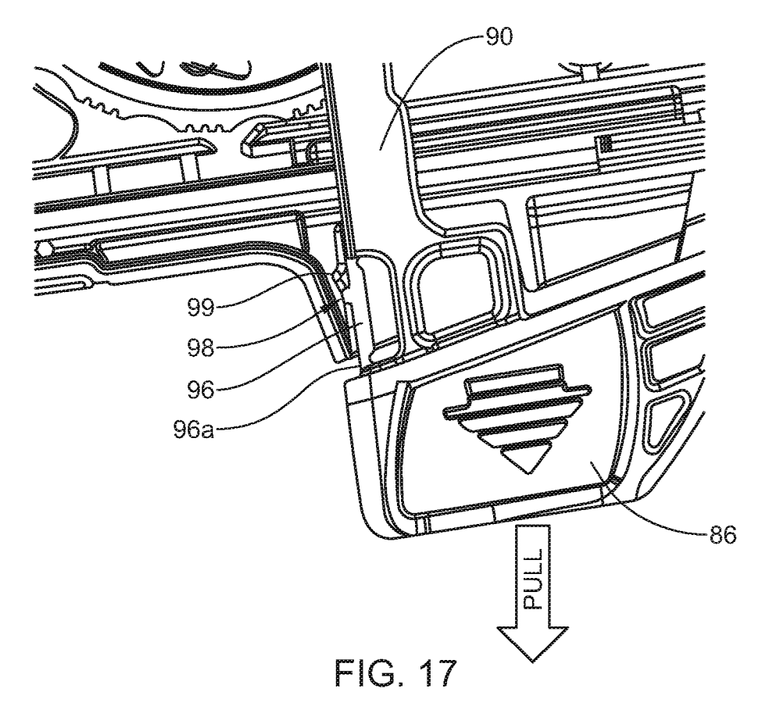

As depicted in FIGS. 3, 12, 14 and 15, the trailing thumbwheel constraint 90 includes a lock detent 92 depending radially outwardly therefrom which is received within one of the radial recesses 94 of the thumbwheel 44 thereby also preventing rotational movement of the thumbwheel 44 prior to removal of the lock pin and/or during use. The trailing thumbwheel constraint 90 passes through the gap 82 (identified hereinabove) extending through the handle frame 32 and through at least one of the channels 80. In one embodiment, best depicted in FIGS. 16 and 17, the lock member 84 includes a forward or leading facing lock spring or pin 96 which may be in the form of a living hinge or spring. The lock spring 96 may be connected at one or both of its ends to the lock member 84. The lock spring 96 includes a lock pin detent 98 which is received within a corresponding capture groove 99 in the handle frame 32 to secure the lock member 84 relative to the handle 12 (e.g., the lock or secured position of the lock member 84) as depicted in FIG. 16. To release the lock member 84, the manually engageable segment 86 is pulled downwardly causing the lock pin 96 to deflect inwardly toward the central area of the lock member 84 about the living hinge 96a of the lock spring 96. In this release position of the lock member 84 depicted in FIG. 17, the lock pin detent 98 is released from the capture groove 99 thereby permitting downward removal of the lock member 84 from the handle 12. Other arrangements for releasably securing the lock member 84 relative to the handle 12 are envisioned.

The operation of the stent delivery system 10 will now be discussed. Saline may be introduced through the luer connector 26 to perform a flushing function through the lumen of the inner member 20. A guidewire is positioned to access the targeted intravascular site, e.g., a stenotic region. The elongated catheter 14 of the stent delivery system 10 is advanced along the guidewire to position the stent 100 adjacent the stenotic region. Confirmation of the proper location is ascertained through imaging of the stent 100 and/or imaging the radiopaque markers located on the inner member 20, the stop member 22 and/or the outer member 24 of the catheter. Thereafter, the lock member 84 is removed from the handle 12. The thumbwheel 44 is rotated causing the outer clip 62, e.g., the wings 76 to traverse the channels 80 (including across the gap 82) and the outer member 24 to retract. During retraction of the outer member 24, the stent 100 remains in contacting or abutting engagement with the distal end of the stop member 22 preventing longitudinal movement of the stent 100. Continued rotation of the thumbwheel 44 and retraction of the outer member 24 causes release of the stent 100 within the stenotic region. The handle 12 may be rotated by the clinician to aid in placement of the catheter 14 without effecting functioning of the deployment mechanism.

As discussed hereinabove, the mechanical advantage and increased velocity ratio provided by the deployment mechanism will provide rapid longitudinal translation of the outer member 24 to expose the stent 100 to effect proper placement of the stent 100 in e.g., the venous system.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A medical device delivery system comprising:
a handle defining a channel;
an elongate catheter extending from the handle, the elongate catheter comprising:
an inner member; and
an outer member mounted about the inner member and configured for longitudinal movement, relative to the inner member, from an extended position to a retracted position;
a medical device mounted about the inner member;
a thumbwheel mounted to the handle, the thumbwheel being configured for rotational movement to cause corresponding movement of the outer member from the extended position to the retracted position;
a clip connected to the outer member, the clip comprising an anti-rotation wing configured to be received within the channel, traverse the channel in response to rotation of the thumbwheel, and prevent rotational movement of the outer member relative to the handle; and
a pull cable extending about a hub of the thumbwheel, a first end of the pull cable being coupled to the clip and a second end of the pull cable being coupled to the thumbwheel, wherein an intermediate section of the pull cable between the first end and the second end extends about a pulley disposed within the handle,
wherein the clip defines an opening configured to receive the intermediate section of the pull cable, and wherein the first end of the pull cable includes a ball segment configured to engage with the clip to retain the intermediate section of the pull cable within the opening, wherein the ball segment of the pull cable is secured to the clip by least one of a mechanical interlock, an adhesive, welding, swaging, or insert molding.

2. The medical device delivery system of claim 1, wherein the anti-rotation wing comprises a pair of diametrically opposed anti-rotation wings and the channel comprises a pair of channels, wherein each anti-rotation wing of the diametrically opposed anti-rotation wings is configured to be received within a respective channel of the pair of channels.

3. The medical device delivery system of claim 1, wherein the medical device comprises a stent configured to expand from a constrained configuration to an expanded configuration upon movement of the outer member toward the retracted position, the elongate catheter further comprising a stop member mounted about the inner member, the stop member dimensioned to engage the stent to minimize longitudinal movement of the stent relative to the inner member upon movement of the outer member from the extended position toward the retracted position.

4. The medical device delivery system of claim 1, wherein the clip further comprises a cylindrical mount configured to receive a trailing end of the outer member.

5. The medical device delivery system of claim 1, wherein the thumbwheel is connected to the outer member, the medical device delivery system further comprising a ratchet comprising a ratchet spring mounted to the handle, the ratchet spring engageable with ratchet teeth defined within the thumbwheel, and wherein the ratchet is configured to permit selective incremental movement of the thumbwheel in a first rotational direction corresponding to movement of the outer member toward the retracted position while preventing movement of the thumbwheel in a second rotational direction opposite the first rotational direction.

6. The medical device delivery system of claim 1, further comprising a lock member releasably mountable to the handle, wherein the lock member is configured to engage the thumbwheel to prevent rotational movement of the thumbwheel when the lock member is secured relative to the handle and configured to release the thumbwheel when the lock member is released relative to the handle.

7. The medical device delivery system of claim 6, wherein the clip further comprises a lock wall distal to a proximal end of the anti-rotation wing, the lock member including a clip restraint configured to engage with the lock wall of the clip to prevent movement of the outer member from the extended position to the retracted position when the lock member is secured relative to the handle to prevent longitudinal movement of the clip and the outer member.

8. The medical device delivery system of claim 7, wherein the thumbwheel includes a radial surface defining a plurality of radial recesses, wherein each radial recess of the plurality of radial recesses is defined by a closed boundary, is spaced from an adjacent radial recess of the plurality of radial recesses, and is separated from the adjacent radial recess by the radial surface, and wherein the lock member comprises a trailing thumbwheel constraint having a lock detent, the lock detent being dimensioned and configured to be received within a radial recess of the plurality of radial recesses of the thumbwheel to prevent rotational movement of the thumbwheel when the lock member is secured relative to the handle.

9. The medical device delivery system of claim 8, wherein the handle comprises a handle frame defining a gap on a first side of the handle frame and the thumbwheel protrudes through a second side of the handle frame different than the first side, and wherein the lock member is configured to extend through the gap to engage the lock detent with the radial recess.

10. The medical device delivery system of claim 1, wherein the anti-rotation wing is positioned at a proximal end of the clip.

11. A stent delivery system, comprising:
a handle defining a channel;
a pulley disposed within the handle;
an elongate catheter extending from the handle, the elongate catheter comprising:
an inner member;
an outer member mounted about the inner member and configured for longitudinal movement from an extended position to a retracted position; and
a stent mounted about the inner member;
a thumbwheel mounted to the handle and connected to the outer member, the thumbwheel being comprising a hub and configured for rotational movement to cause corresponding movement of the outer member from the extended position to the retracted position;
a clip connected to the outer member, the clip comprising an anti-rotation wing configured to be received within the channel, traverse the channel in response to rotation of the thumbwheel, and prevent rotational movement of the outer member relative to the handle; and
a pull cable connecting the clip and the thumbwheel, wherein the pull cable extends about the hub of the thumbwheel and the pulley disposed within the handle, a first end of the pull cable being coupled to the clip and a second end of the pull cable being coupled to the thumbwheel,
wherein the clip defines an opening configured to receive an intermediate section of the pull cable between the first end and the second end, and wherein the first end of the pull cable includes a ball segment configured to engage with the clip to retain the intermediate section of the pull cable within the opening, wherein the ball segment of the pull cable is secured to the clip by least one of a mechanical interlock, an adhesive, welding, swaging, or insert molding.

12. The stent delivery system of claim 11, wherein the anti-rotation wing comprises a pair of diametrically opposed anti-rotation wings and the channel comprises a pair of channels, wherein each anti-rotation wing of the diametrically opposed anti-rotation wings is configured to be received within a respective channel of the pair of channels of the handle.

13. The stent delivery system of claim 11, wherein the stent is configured to expand from a constrained configuration to an expanded configuration upon movement of the outer member toward the retracted position, the elongate catheter further comprising a stop member mounted about the inner member, the stop member dimensioned to engage the stent to minimize longitudinal movement of the stent relative to the inner member upon movement of the outer member from the extended position toward the retracted position.

14. The stent delivery system of claim 11, further comprising a ratchet comprising a ratchet spring mounted to the handle, the ratchet spring engageable with ratchet teeth defined within the thumbwheel, and wherein the ratchet is configured to permit selective incremental movement of the thumbwheel in a first rotational direction corresponding to movement of the outer member toward the retracted position while preventing movement of the thumbwheel in a second rotational direction opposite the first rotational direction.

15. The stent delivery system of claim 11, further comprising a lock member releasably mountable to the handle, wherein the lock member is configured to engage the thumbwheel to prevent rotational movement of the thumbwheel when the lock member is secured relative to the handle and configured to release the thumbwheel when the lock member is released relative to the handle.

16. The stent delivery system of claim 11, wherein the clip further comprises a lock wall distal to a proximal end of the anti-rotation wing, the stent delivery system further comprising a lock member including a clip restraint configured to engage with the lock wall of the clip to prevent movement of the outer member from the extended position to the retracted position when the lock member is secured relative to the handle to prevent longitudinal movement of the clip and the outer member.

17. The stent delivery system of claim 16, wherein the thumbwheel includes a radial surface defining a plurality of radial recesses, wherein each radial recess of the plurality of radial recesses is defined by a closed boundary, is spaced from an adjacent radial recess of the plurality of radial recesses, and is separated from the adjacent radial recess by the radial surface, and wherein the lock member comprises a trailing thumbwheel constraint having a lock detent, the lock detent being dimensioned and configured to be received within a radial recess of the plurality of radial recesses of the thumbwheel to prevent rotational movement of the thumbwheel when the lock member is secured relative to the handle.

18. A method comprising:
advancing an elongate catheter of a medical device delivery system through a body lumen of a patient, the medical device delivery system comprising:
a handle defining a channel;
the elongate catheter extending from the handle, the elongate catheter comprising:
an inner member; and
an outer member mounted about the inner member and configured for longitudinal movement, relative to the inner member, from an extended position to a retracted position;
a medical device mounted about the inner member;
a thumbwheel mounted to the handle, the thumbwheel being configured for rotational movement to cause corresponding movement of the outer member from the extended position to the retracted position;
a clip connected to the outer member, the clip comprising an anti-rotation wing configured to be received within the channel, traverse the channel in response to rotation of the thumbwheel, and prevent rotational movement of the outer member relative to the handle; and
a pull cable extending about a hub of the thumbwheel, a first end of the pull cable being coupled to the clip and a second end of the pull cable being coupled to the thumbwheel, wherein an intermediate section of the pull cable between the first end and the second end extends about a pulley disposed within the handle,
wherein the clip defines an opening configured to receive the intermediate section of the pull cable, and wherein the first end of the pull cable includes a ball segment configured to engage with the clip to retain the intermediate section of the pull cable within the opening, wherein the ball segment of the pull cable is secured to the clip by least one of a mechanical interlock, an adhesive, welding, swaging, or insert molding; and
rotating the thumbwheel to cause the outer member to move from the extended position toward the retracted position, thereby causing the medical device to expand from the constrained configuration to an expanded configuration within the body lumen.

19. The method of claim 18, wherein the medical device delivery system further comprises a lock member configured to engage the thumbwheel to prevent movement of the thumbwheel when the lock member is secured relative to the handle and configured to release the thumbwheel when the lock member is released relative to the handle, the method further comprising releasing the lock member from the handle before rotating the thumbwheel to cause the outer member to move from the extended position toward the retracted position.

* * * * *